(12) United States Patent
Lifshitz

(10) Patent No.: US 6,350,870 B2
(45) Date of Patent: Feb. 26, 2002

(54) PROCESS FOR PREPARING PURE CRYSTALLINE LORAZEPAM

(75) Inventor: Igor Lifshitz, Petah Tiqva (IL)

(73) Assignee: Teva Pharmaceutical Industreis, Ltd., Petah Tiqva (IL)

( * ) Notice: Subject to any disclaimer, the term of this patent is extended or adjusted under 35 U.S.C. 154(b) by 0 days.

(21) Appl. No.: 09/799,318

(22) Filed: Mar. 5, 2001

Related U.S. Application Data

(60) Provisional application No. 60/187,990, filed on Mar. 6, 2000.

(51) Int. Cl.⁷ .................. C07D 243/24; C07D 243/26
(52) U.S. Cl. ........................................... 540/507
(58) Field of Search ......................................... 540/507

(56) References Cited

U.S. PATENT DOCUMENTS 3,296,249 A    1/1967    Bell .................. 260/239.3

*Primary Examiner*—Bruck Kifle
(74) *Attorney, Agent, or Firm*—Kenyon & Kenyon

(57) ABSTRACT

The present invention provides a process for preparing crystalline lorazepam substantially free of bound solvent from a lorazepam alcohol solvate or hydrate by suspending the lorazepam solvate in an organic medium selected from ethyl acetate, cyclohexane, dichloromethane, toluene and mixtures thereof. This process is useful in producing the anti-anxiety and sedative agent lorazepam in increased yields. A process for converting lorazepam lower alcohol solvates to lorazepam hydrate is also disclosed.

49 Claims, No Drawings

PROCESS FOR PREPARING PURE CRYSTALLINE LORAZEPAM

CROSS-REFERENCE TO RELATED APPLICATIONS

This application claims the benefit of provisional application Serial No. 60/187,990, filed Mar. 6, 2000, which is incorporated herein by reference.

FIELD OF THE INVENTION

The present invention relates to desolvation processes and, in particular, to a process for desolvating lorazepam lower alcohol solvates and lorazepam hydrate.

BACKGROUND OF THE INVENTION

The first benzodiazepine sedative, chlordiazepoxide, was introduced as a treatment for anxiety in humans after the discovery of its "taming" effect on animals in the 1950's. Since that time, a large number of benzodiazepines have been found to possess sedative, anti-convulsant, and muscle-relaxant properties. Benzodiazepines are used clinically to treat a variety of ailments, including depression, anxiety, insomnia and muscle spasms.

Lorazepam is a benzodiazepine with anti-anxiety and sedative effects that is widely used for treating human anxiety disorders and for pre-operative sedation. Lorazepam is the generic name of the compound 7-chloro-5-(o-chlorophenyl)-1,3-dihydro-3-hydroxy-2H-1,4-benzodiazepin-2-one.

U.S. Pat. No. 3,296,249, which is incorporated herein by reference, describes a process for preparing lorazepam. In the last step of that process, the acetyl group is removed from 3-acetoxy-7-chloro-5-(o-chlorophenyl)-1,3-dihydro-2H-1,4-benzodiazepin-2-one by treatment with sodium hydroxide in ethanol. The resulting lorazepam solution is allowed to stand until a precipitate is formed. The precipitate is then filtered, washed with water, and recrystallized from ethanol. Although the process for making lorazepam disclosed in the '249 patent is efficient, the precipitated product of the last step of the process is a one-to-one ethanol solvate of lorazepam which must be desolvated before it can be incorporated into a pharmaceutical for administration to humans. Substitution of solvents that do not form solvates with lorazepam in the last step of the '249 patent is not practical due to solubility problems.

Lorazepam's poorly solubility in solvents commonly used by the pharmaceutical industry makes subsequent processing to desolvate the lorazepam problematic. Heating of lorazepam ethanol solvate to drive off the ethanol is not effective, demands prolonged thermal treatment and may cause partial chemical decomposition. There is a need for a process that removes the alcohol from a lorazepam alcohol solvate and yields lorazepam in a crystalline state.

SUMMARY OF THE INVENTION

It has been found that water and lower alcohol molecules of solvation can be removed from lorazepam solvates by suspending the solvate in certain organic solvents and organic solvent mixtures. An advantage of the most preferred embodiments of the invention is that they use a minimum of solvent, which is advantageous because it keeps the cost of the process down and maximizes the recovery of desolvated crystalline lorazepam.

Ethanol, methanol or water bound to lorazepam can be removed by contacting the lorazepam solvate with ethyl acetate or a mixture of ethyl acetate/cyclohexane or dichloromethane or toluene or a mixture of ethyl acetate and toluene, or a mixture of dichloromethane and toluene.

It also has been found that lorazepam lower alcohol solvates can be converted to lorazepam hydrate by suspending the solvate in water under conditions that convert it to lorazepam hydrate.

If desired, the two processes can be combined to convert lower alcohol solvates of lorazepam into crystalline lorazepam substantially free of bound solvent by first converting the lower alcohol solvate into lorazepam hydrate and then converting lorazepam hydrate into crystalline anhydrous lorazepam.

DETAILED DESCRIPTION OF THE PREFERRED EMBODIMENTS

The present invention provides a new process for preparing pure crystalline lorazepam from a lower alcohol solvate of lorazepam or lorazepam hydrate (collectively "lorazepam solvates"). "Lower alcohol" means an alcohol having from 1 to 4 carbon atoms and therefore includes methanol, ethanol and isopropanol.

Suspending the lorazepam solvate in certain liquid organic media can be used to desolvate the lorazepam and enables isolation of lorazepam in a crystalline state that is substantially free of bound solvent. The desolvation may be accelerated by heating the suspension to an elevated temperature. After the lorazepam is desolvated of alcohol or water, it is separated from the liquid organic medium by, for example, filtration or decantation. The lorazepam may then be washed and dried by conventional means.

A suitable liquid organic medium is an organic compound that is liquid at room temperature and, in particular, is ethyl acetate, cyclohexane, dichloromethane, toluene and mixtures thereof Preferred liquid organic media are ethyl acetate, mixtures of ethyl acetate and cyclohexane, dichloromethane, toluene, mixtures of ethyl acetate and toluene, and mixtures of dichloromethane and toluene. The invention is further illustrated with ethyl acetate, dichloromethane, mixtures of ethyl acetate with cyclohexane and mixtures of dichloromethane with toluene.

In one embodiment, the lorazepam solvate is suspended in ethyl acetate in an amount of about 3 to about 5 milliliters of ethyl acetate per gram of lorazepam, most preferably about 4 ml/g. The desolvation may be conducted at any temperature between about 20° C. and 80° C. Preferably, the suspension is heated to an elevated temperature of from about 55° C. to about 65° C. with mechanical agitation, e.g. stirring. Depending upon the temperature, desolvation can take from 5 minutes to about 24 h. When the suspension is stirred at 60° C. the lorazepam desolvates in about an hour. The suspension is then cooled most preferably to a temperature in the range of from about 15° C. to about 20° C. After the suspension is cooled, the desolvated lorazepam crystals may be separated from the liquid organic medium by filtration or decantation. The desolvated lorazepam is then washed with a solvent; dichloromethane, cyclohexane, toluene, xylene, chloroform, pentane, dichloroethane, hexane, heptane, and ethyl acetate being preferred, with ethyl acetate being most preferred. The washed desolvated lorazepam can be dried at a temperature in the range of from about 20° C. to about 90° C., more preferably in the range of from about 40° C. to about 60° C., and most preferably at a temperature of about 50° C., either at ambient pressure or under vacuum.

According to another embodiment, the lorazepam solvate is suspended in a mixture of ethyl acetate and cyclohexane.

Addition of an equal amount of cyclohexane to a suspension of the lorazepam solvate in ethyl acetate eases stirring and improves recovery of desolvated lorazepam (compare Examples 1 and 2). Preferably, the ratio of ethyl acetate to cyclohexane is from about 1000:1 to about 1:3, more preferably from about 1:2 to about 2:1 and most preferably about 1:1; and the ratio of lorazepam solvate to the mixture of ethyl acetate and cyclohexane is from about 1:3 (g:ml) to about 1:20 (g:ml), and most preferably from about 1:4 to about 1:8. The suspension is preferably heated to about 40° C. to about 80° C., more preferably about 50° C. to about 70° C. Desolvation occurs in about an hour when the suspension is heated to 50–70° C.

According to another illustrative embodiment, the lorazepam solvate is suspended in dichloromethane. The ratio of lorazepam solvate to dichloromethane is preferably from about 1:2 (g:ml) to about 1:100 (g:ml), and most preferably from about 1:4 to about 1:8. The suspension is stirred for several hours. If the suspension is heated to a temperature of about 40° C. the desolvation is substantially complete in about an hour.

In yet another embodiment, the lorazepam solvate is suspended in a mixture of dichloromethane and toluene. Preferred dichloromethane and toluene mixtures contain dichloromethane and toluene in a ratio of from about 1:1000 to about 1000:1 (v:v), i.e. about any ratio is well suited, with a preferred mixture having about a 1:1 ratio of dichloromethane to toluene. The ratio of lorazepam solvate to the dichloromethane/toluene mixture is preferably from about 2 to about 100 milliliters of the mixture per gram of lorazepam solvate.

Heated suspensions should be cooled as described with reference to the ethyl acetate suspension before isolating the lorazepam. Lorazepam substantially free of bound solvent may be isolated from suspension in ethyl acetate/cyclohexane mixtures, dichloromethane, dichloromethane/toluene mixtures and other suitable liquid organic media, washed and dried by the techniques described with reference to desolvation by suspension in ethyl acetate.

Lorazepam obtained from these suspensions contains less than 0.5% of the lower alcohol or water of solvation present in the starting material.

The invention also provides a new process for preparing lorazepam hydrate from lorazepam lower alcohol solvates by suspending the lower alcohol solvate in water. Preferably, the ratio of lorazepam lower alcohol solvate to water is from about 1:2 to 1:1000, and most preferably from about 1:3 to 1:10. According to a particularly preferred set of conditions for converting a lower alcohol solvate of lorazepam to the lorazepam hydrate, the lower alcohol solvate is added to water in an amount of about 0.2 grams per milliliter and is stirred for about 0.2 to about 1 hour at 10° C. to 80° C. If heated, the suspension is then cooled preferably to a temperature in the range of from about 0° C. to about 25° C., and the lorazepam hydrate is washed with water. The washed lorazepam hydrate is dried for about 1 hour to about 20 hours at a temperature in the range of from about 20° C. to about 90° C., more preferably in the range of from 40° C. to 60° C. and most preferably at 50° C., either at ambient pressure or under vacuum.

Having thus described the present invention with reference to certain preferred embodiments, the following examples are provided to further illustrate the processes by which crystalline lorazepam substantially free of bound solvent may be obtained. One skilled in the art will recognize variations and substitutions in the processes as described and exemplified which do not depart from the spirit and scope of the invention as defined by the claims.

EXAMPLES

Example 1

Lorazepam ethanol solvate (5 kg) was suspended in ethyl acetate (20 L). The suspension was heated to 60° C. for one hour with rapid stirring and then cooled to 15° C. The suspension was filtered to recover the lorazepam crystals. The crystals were then washed with ethyl acetate (2L) and dried at 50° C. under 65 mm Hg vacuum for two hours to give crystalline lorazepam (3.8 kg, 80%).

Example 2

Lorazepam ethanol solvate (100 g) was suspended in a 1:1 mixture of ethyl acetate and cyclohexane (800 ml). The suspension was heated to 60° C. for 1 hour with rapid stirring and then cooled to 15° C. The cooled suspension was filtered to recover the lorazepam crystals and the crystals were then washed with ethyl acetate (20 ml). The crystals were dried at 50° C. under 65 mm Hg vacuum for two hours to give crystalline lorazepam (85 g, 90%).

Example 3

Lorazepam ethanol solvate (100 g) was suspended in a 1:1 mixture of ethyl acetate and toluene (400 ml). The suspension was heated to 60° C. for 1 hour with rapid stirring and then cooled to 15° C. The suspension was filtered to recover the lorazepam. The lorazepam crystals were then washed with ethyl acetate (20 ml) and dried under 65 mm Hg vacuum at about 50° C. for about two hours to give crystalline lorazepam (83 g) in 88% yield.

Example 4

Lorazepam ethanol solvate (100 g) was suspended in dichloromethane (600 ml). The suspension was heated to about 40° C. for 1 hour with rapid stirring and then cooled to 10° C. The suspension was filtered to recover the lorazepam crystals. The crystals were washed with dichloromethane (20 ml) and dried at 50° C. under 65 mm Hg vacuum for two hours to give crystalline lorazepam (85.5 g, 90%).

Example 5

Lorazepam ethanol solvate (100 g) was suspended in a 1:1 mixture of dichloromethane and toluene (600 ml). The suspension was then heated to 25 ° C. for one hour and then cooled to 15° C. The suspension was filtered to recover the lorazepam crystals. The crystals were washed with toluene (20 ml) and dried at 50° C. under 65 mm Hg vacuum for two hours to give crystalline lorazepam (85 g, 90%)

Example 6

Lorazepam methanol solvate (100 g) was suspended in ethyl acetate (400 ml). The suspension was heated to 60° C. for one hour with rapid stirring and then cooled to 15° C. The suspension was filtered to recover the lorazepam crystals. The crystals were washed with ethyl acetate (50 ml) and dried at 50° C. under 65 mm Hg vacuum for two hours to give crystalline lorazepam (85 g, 80%).

Example 7

Lorazepam ethanol solvate (100 g) was suspended in water (500 ml). The suspension was rapidly stirred at room temperature for 1 hour and then filtered to recover lorazepam hydrate. The hydrate crystals were washed with water (100 ml) and dried at 50° C. under 65 mm Hg vacuum for 5 h to give lorazepam hydrate (90%).

Example 8

Lorazepam hydrate (100 g) was suspended in ethyl acetate (400 ml). The slurry was heated to 60° C. for 1 hour with rapid stirring and then cooled to 15° C. The suspension was filtered to recover the lorazepam crystals. The crystals were then washed with ethyl acetate (50 ml) and dried at 50° C. under 65 mm Hg vacuum for four hours to give crystalline lorazepam (80 g, 85%).

What is claimed is:

1. A process for preparing crystalline lorazepam substantially free of bound solvent from a lorazepam solvate with water or a lower alcohol comprising the steps of suspending the lorazepam solvate in a liquid organic medium selected from the group consisting of ethyl acetate, cyclohexane, toluene, dichloromethane and mixtures thereof under conditions effective to desolvate the lorazepam and isolating crystalline lorazepam substantially free of bound solvent from the suspension.

2. The process of claim 1 wherein the bound solvent is water.

3. The process of claim 1 wherein the bound solvent is methanol, ethanol or isopropanol.

4. The process of claim 3 wherein the bound solvent is ethanol.

5. The process of claim 1 wherein the liquid organic medium is ethyl acetate.

6. The process of claim 5 wherein the ethyl acetate is used in an amount of from about 2 to about 10 milliliters per gram of lorazepam solvate.

7. The process of claim 6 wherein the ethyl acetate is used in an amount of from about 3 to about 5 milliliters per gram of lorazepam solvate.

8. The process of claim 7 wherein the ethyl acetate is used in an amount of about 5 milliliters per gram of lorazepam solvate.

9. The process of claim 1 wherein the liquid organic medium is a mixture of ethyl acetate and cyclohexane.

10. The process of claim 9 wherein the liquid organic medium is a mixture of cyclohexane and ethyl acetate in a volume ratio of from about 1 volume of cyclohexane to 2 volumes of ethyl acetate to about 2 volumes of cyclohexane to 1 volume of ethyl acetate.

11. The process of claim 10 wherein the volume ratio of ethyl acetate to cyclohexane is about 1:1.

12. The process of claim 9 wherein the liquid organic medium is used in an amount of from about 3 to about 20 milliliters per gram of lorazepam solvate.

13. The process of claim 12 wherein the liquid organic medium is used in an amount of from about 4 to about 8 milliliters per gram of lorazepam solvate.

14. The process of claim 1 wherein the liquid organic medium is dichloromethane.

15. The process of claim 14 wherein the dichloromethane is used in an amount of from about 2 to about 100 milliliters per gram of lorazepam solvate.

16. The process of claim 15 wherein the dichloromethane is used in an amount of from about 4 to about 8 milliliters per gram of lorazepam solvate.

17. The process of claim 1 wherein the liquid organic medium is a mixture of dichloromethane and toluene.

18. The process of claim 17 wherein the liquid organic medium is a mixture of dichloromethane and toluene in a volume ratio of from about 1 volume of dichloromethane to 1000 volumes of toluene to about 1000 volumes of dichloromethane to 1 volume of toluene.

19. The process of claim 18 wherein the volume ratio of dichloromethane and toluene is about 1 to 1.

20. The process of claim 17 wherein the liquid organic medium is used in an amount of from about 2 to about 100 milliliters per gram of lorazepam solvate.

21. The process of claim 1 wherein the conditions effective for desolvating the lorazepam include heating the suspension to an elevated temperature.

22. The process of claim 21 wherein the elevated temperature is in the range of from about 40° C. to about 80° C.

23. The process of claim 22 wherein the liquid organic medium is ethyl acetate and the elevated temperature is in the range of from about 55° C. to about 65° C.

24. The process of claim 22 wherein the liquid organic medium is a mixture of ethyl acetate and cyclohexane and the elevated temperature is in a range of from about 50° C. to about 70° C.

25. The process of claim 21 wherein the liquid organic medium is dichloromethane and the elevated temperature is about 42° C. or a lower temperature.

26. The process of claim 21 wherein the liquid organic medium is a mixture of dichloromethane and toluene and the elevated temperature is about 80° C. or lower temperature.

27. The process of claim 26 wherein the elevated temperature is about 60° C.

28. The process of claim 21 further comprising the step of cooling the suspension from elevated temperature before isolating the crystalline lorazepam substantially free of bound alcohol from the suspension.

29. The process of claim 28 wherein the suspension is cooled to a temperature in the range of from about 0° C. to about 50° C. before isolating the crystalline lorazepam substantially free of bound alcohol from the suspension.

30. The process of claim 29 wherein the cooling temperature is in the range of from about 15° C. to about 20° C.

31. The process of claim 1 wherein the crystalline lorazepam substantially free of bound alcohol is isolated by filtering the suspension and recovering lorazepam crystals on the filter and wherein the process further includes washing the lorazepam crystals and drying them.

32. The process of claim 31 wherein the wash solvent is selected from the group consisting of dichloromethane, cyclohexane, toluene, xylene, chloroform, pentane dichloroethane, hexane, heptane and ethyl acetate.

33. The process of claim 31 wherein the lorazepam crystals are dried at a temperature in the range of from about 20° C. to about 80° C.

34. The process of claim 33 wherein the lorazepam crystals are dried at a temperature in the range of from about 40° C. to about 60° C.

35. The process of claim 31 wherein the lorazepam crystals are dried under vacuum.

36. A process for desolvating a lorazepam solvate with water or a lower alcohol comprising the steps of suspending the lorazepam solvate in ethyl acetate in an amount of from about 2 to about 10 milliliters of ethyl acetate per gram of lorazepam solvate, heating the suspension to a temperature of from about 55° C. to about 65° C. for a time sufficient to desolvate the lorazepam, cooling the suspension to a temperature in the range of about 15° C. to about 20° C., and separating the ethyl acetate either by filtration or decantation, and then drying the lorazepam to obtain crystalline lorazepam free of bound solvent.

37. A process for desolvating a lorazepam solvate with water or a lower alcohol comprising the steps of suspending the lorazepam solvate in a liquid organic medium comprising ethyl acetate and cyclohexane in an amount of from about 3 to about 20 milliliters of the liquid organic medium per gram of lorazepam solvate, heating the suspension to a temperature of from about 50° C. to about 70° C. for a time sufficient to desolvate the lorazepam, cooling the suspension to a temperature in the range of about 15° C. to about 20° C., and separating the liquid organic medium from the lorazepam either by filtration or decantation, and then drying the lorazepam to obtain crystalline lorazepam free of bound solvent.

38. A process for desolvating a lorazepam solvate with water or a lower alcohol comprising the steps of suspending the lorazepam solvate in dichloromethane in an amount of from about 2 to about 100 milliliters of dichloromethane per gram of lorazepam solvate for a time sufficient to desolvate the lorazepam, with optional heating of the suspension to a temperature in the range of from about 25° C. to about 42° C. and optionally cooling the suspension to a temperature in the range of about 15° C. to about 20° C., and separating the dichloromethane either by filtration or decantation, and then drying the lorazepam to obtain crystalline lorazepam free of bound solvent.

39. A process for desolvating a lorazepam solvate with water or a lower alcohol comprising the steps of suspending the lorazepam solvate in a liquid organic medium comprising dichloromethane and toluene in an amount of from about 2 to about 100 milliliters of liquid organic medium per gram of lorazepam solvate, heating the suspension to a temperature of from about 25° C. to about 60° C. for a time sufficient to desolvate the lorazepam, cooling the suspension to a temperature in the range of about 15° C. to about 20° C., and separating the liquid organic medium either by filtration or decantation, and then drying the lorazepam to obtain crystalline lorazepam free of bound solvent.

40. A process for preparing lorazepam hydrate from a lorazepam lower alcohol solvate comprising the steps of suspending the lorazepam lower alcohol solvate in water under conditions effective to substantially convert the suspended lorazepam lower alcohol solvate to lorazepam hydrate and then isolating lorazepam hydrate from the aqueous suspension.

41. The process of claim 40 wherein the water is used in an amount of from about 2 milliliters to about 1000 milliliters per gram of lorazepam lower alcohol solvate.

42. The process of claim 41 wherein the water is used in an amount of from about 3 milliliters to about 10 milliliters per gram of lorazepam lower alcohol solvate.

43. The process of claim 42 wherein the water is used in an amount of about 5 milliliters per gram of lorazepam lower alcohol solvate.

44. The process of claim 40 wherein the conditions effective for converting the suspended lorazepam lower alcohol solvate to lorazepam hydrate include adjusting the temperature of the suspension to from about 10° C. to about 80° C.

45. The process of claim 44 wherein the suspension is heated to an elevated temperature of from about 30° C. to about 80° C.

46. The process of claim 45 further comprising the step of cooling the aqueous suspension from the elevated temperature before isolating the lorazepam hydrate from the aqueous suspension.

47. The process of claim 46 wherein the lorazepam hydrate is isolated from the aqueous suspension by filtering the aqueous suspension and recovering the lorazepam hydrate on the filter and wherein the process further comprises the steps of washing and drying the lorazepam hydrate.

48. The process of claim 47 wherein the lorazepam hydrate is dried at a temperature in the range of from about 40° C. to about 80° C.

49. The process of claim 48 wherein the lorazepam hydrate is dried under vacuum.

* * * * *